United States Patent [19]
Daugherty

[11] Patent Number: 5,695,474
[45] Date of Patent: Dec. 9, 1997

[54] NEEDLE SHIELD WITH COLLAPSIBLE COVER

[75] Inventor: Charles W. Daugherty, Sandy, Utah

[73] Assignee: Becton Dickinson and Company, Franklin Lakes, N.J.

[21] Appl. No.: 781,549

[22] Filed: Jan. 9, 1997

Related U.S. Application Data

[63] Continuation of Ser. No. 531,576, Sep. 18, 1995, abandoned.

[51] Int. Cl.$^6$ .................................................... A61M 5/00
[52] U.S. Cl. ................................................ 604/162; 604/263
[58] Field of Search ................................. 604/162, 164, 604/165, 158, 171, 263, 272, 110, 192, 195, 198

[56] References Cited

U.S. PATENT DOCUMENTS

| | | | |
|---|---|---|---|
| 3,867,937 | 2/1975 | Schwartz | 128/221 |
| 3,994,295 | 11/1976 | Wulff | 128/215 |
| 4,702,737 | 10/1987 | Pizzino | 604/191 |
| 4,725,267 | 2/1988 | Vaillancourt | 604/192 |
| 4,747,831 | 5/1988 | Kulli | 604/110 |
| 4,762,516 | 8/1988 | Luther et al. | 604/164 |
| 4,804,372 | 2/1989 | Laico et al. | 604/198 |
| 4,832,696 | 5/1989 | Luther et al. | 604/164 |
| 4,834,718 | 5/1989 | McDonald | 604/195 |
| 4,846,805 | 7/1989 | Sitar | 604/165 |
| 4,897,083 | 1/1990 | Martell | 604/192 |
| 4,921,491 | 5/1990 | Champ | 604/199 |
| 4,927,416 | 5/1990 | Tomkiel | 604/198 |
| 4,935,013 | 6/1990 | Haber et al. | 604/192 |
| 4,944,728 | 7/1990 | Carrell et al. | 604/164 |
| 4,950,250 | 8/1990 | Haber et al. | 604/192 |
| 4,950,252 | 8/1990 | Luther et al. | 604/198 |
| 4,978,344 | 12/1990 | Dombrowski et al. | 604/198 |
| 4,994,041 | 2/1991 | Dombrowski et al. | 604/164 |
| 5,104,384 | 4/1992 | Parry | 604/192 |
| 5,106,379 | 4/1992 | Leap | 604/198 |
| 5,181,524 | 1/1993 | Wanderer et al. | 128/764 |
| 5,219,338 | 6/1993 | Haworth | 664/198 |
| 5,242,416 | 9/1993 | Hutson | 604/192 |
| 5,273,540 | 12/1993 | Luther et al. | 604/110 |
| 5,304,136 | 4/1994 | Erskine et al. | 604/110 |
| 5,332,092 | 7/1994 | Fischer | 206/365 |
| 5,334,149 | 8/1994 | Nortman et al. | 604/110 |
| 5,336,199 | 8/1994 | Castillo et al. | 604/198 |
| 5,374,252 | 12/1994 | Banks et al. | 604/158 |
| 5,376,075 | 12/1994 | Haughton et al. | 604/158 |
| 5,419,766 | 5/1995 | Chang et al. | 604/110 |
| 5,531,713 | 7/1996 | Mastronardi et al. | 604/263 |

FOREIGN PATENT DOCUMENTS

| | | | |
|---|---|---|---|
| 0 576 302 A1 | 12/1993 | European Pat. Off. | A61M 5/32 |
| 0 578 367 A1 | 12/1994 | European Pat. Off. | A61M 26/06 |
| WO 93/11816 | 6/1993 | WIPO . | |

*Primary Examiner*—John D. Yasko
*Attorney, Agent, or Firm*—Eric M. Lee

[57] ABSTRACT

A needle assembly is provided with a collapsible needle shield. In one embodiment of the needle shield assembly, the proximal portion of the handle is formed from a collapsible, non-elastic material. In a second embodiment, the proximal portion of the handle is formed from a telescoping tube that enables complete shielding of the needle when the handle is telescopingly extended. A tip guard is included in both embodiments which resiliently moves over the distal tip of the needle as the shield assembly is fully extended to prevent relative distal movement of the needle after the needle has been withdrawn into the handle.

10 Claims, 6 Drawing Sheets

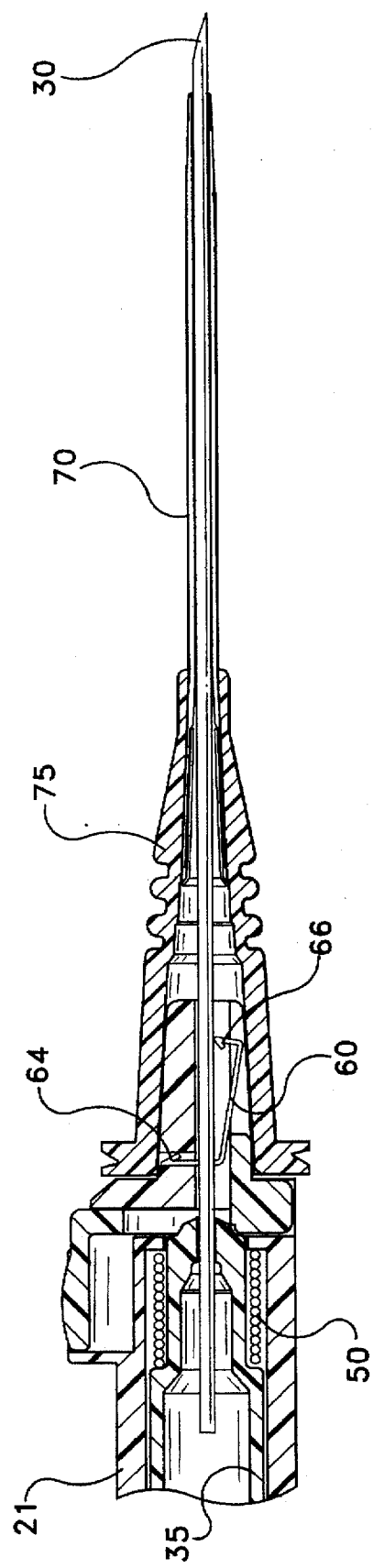
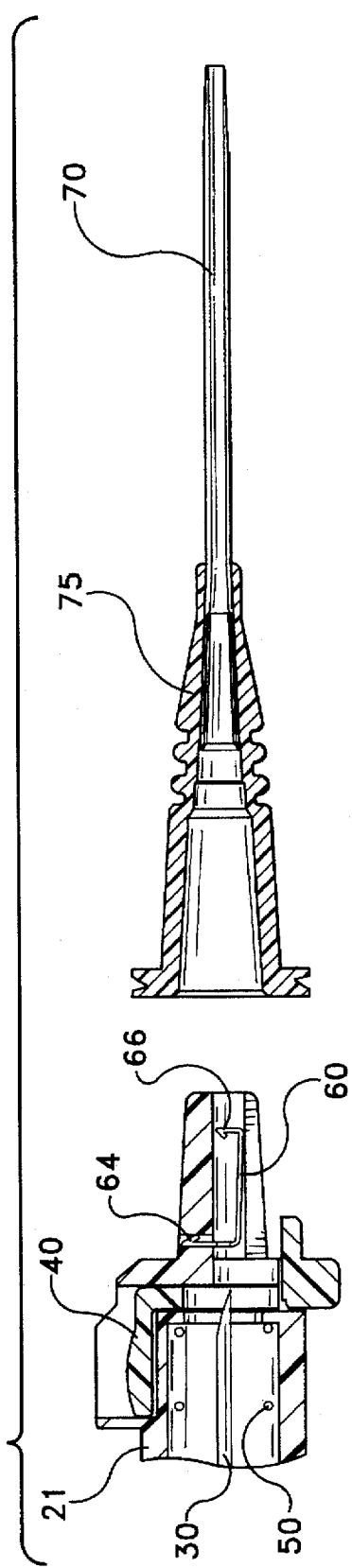

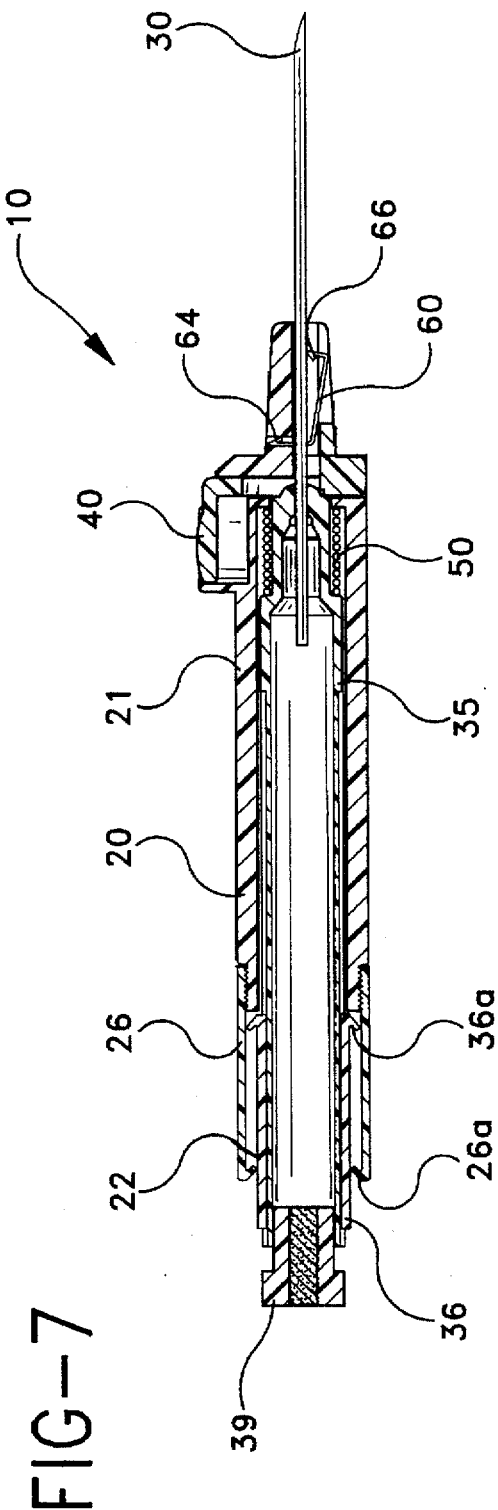
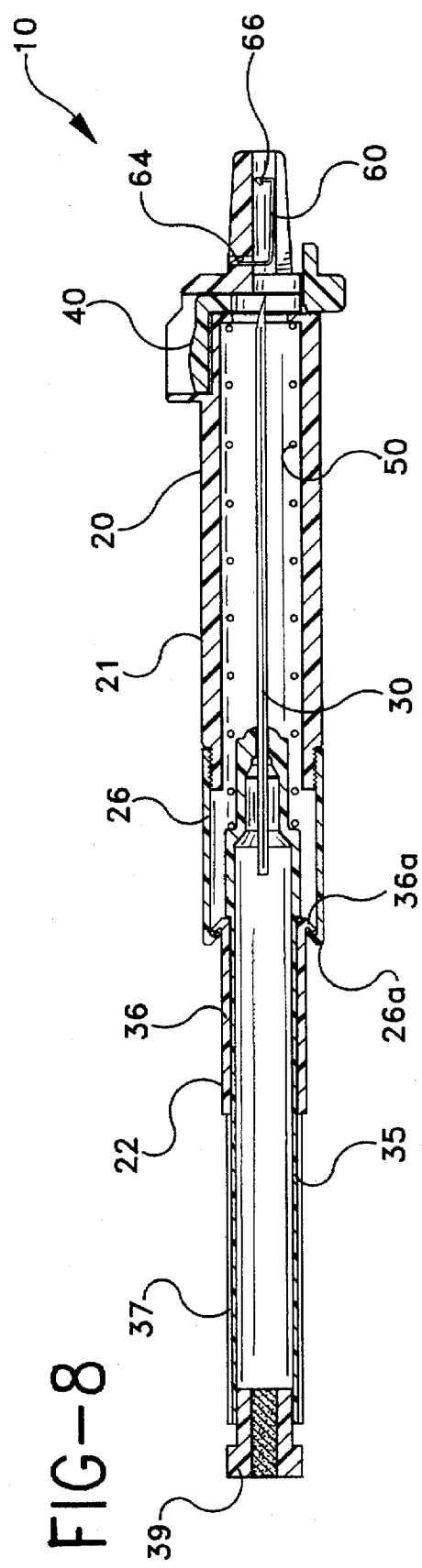

NEEDLE SHIELD WITH COLLAPSIBLE COVER

BACKGROUND OF THE INVENTION

This application is a continuation of application Ser. No. 08/531,576, filed Sep. 18, 1995, now abandoned.

The subject invention relates to a needle shield having a collapsible cover. More particularly, this invention relates to a safety catheter having a collapsible cover that will safely and automatically shield the sharp distal tip of the introducer needle after the needle has been used to place the catheter into a patient.

Sharp needles are typically used in health care procedures as part of a hypodermic needle assembly, a blood collection assembly or an intravenous (IV) catheter assembly. For example, typical IV catheters are initially placed over an introducer needle for insertion into a patient's vein to inject fluid into, withdraw blood from or monitor certain physiological conditions of a patient. After a medical technician inserts the tip of the catheter and introducer needle into a vein, the medical technician advances the catheter completely into the vein and withdraws the introducer needle from the catheter and the patient for disposal.

In recent years, there has been great concern over the immediate disposal of needles after use. This concern has arisen because of the advent of currently incurable and fatal diseases, such as Acquired Immune Deficiency Syndrome ("AIDS"), which can be transmitted by the exchange of body fluids from an infected person to another person. Thus, if a needle has been used to place a catheter in the vein to withdraw blood from or inject fluid into an AIDS infected person, the needle is a vehicle for the transmission of the disease. Thus, it is extremely important for a medical technician to properly dispose of the needle to avoid a needlestick with the contaminated needle. Unfortunately, in certain medical environments, such as emergency situations or as a result of inattention or negligence, needlesticks with a contaminated needle still occur.

In view of the need for a safety device that will protect the medical technician and any personnel in the area from a used needle, a number of needle shields have already been designed. Some shields only cover the sharp distal tip of the needle. This is unsatisfactory in most instances because the shaft of the needle can be the source of contamination from body fluids. Other needle shields have been designed that cover the entire shaft of the needle after use. However, many of these shields are bulky making the device difficult to handle during insertion of the catheter. Thus, there still remains a need to provide a needle shield assembly that is not bulky, that is simple and easy to use and that completely covers the entire needle after use.

SUMMARY OF THE INVENTION

It is therefore an object of this invention to provide a needle shield assembly that is not bulky.

It is another object of this invention to provide a needle shield assembly that is simple and easy to use.

It is yet another object of this invention to provide a needle shield assembly that completely covers the entire needle as well as the sharp distal tip of the needle after use.

Although this invention will be described in connection with an IV catheter introducer needle, it is to be understood that the needle shield assembly of this invention could be used with other needles where shielding of the needle is desirable.

The needle shield assembly of this invention includes a handle having a proximal portion and a distal portion for receiving the needle after use. A needle hub is located inside the handle and has a needle attached at its proximal end to a needle hub. A spring or other biasing mechanism is operatively connected to the needle hub for urging the needle hub and needle toward the proximal portion of the handle. A movable latch engages the needle hub to maintain the needle hub adjacent to the distal portion of the handle with the sharp distal tip of the needle extending beyond the distal portion of the handle until the medical technician desires to shield the needle. A needle tip guard is located in the distal portion of the handle for preventing unwanted distal movement of the needle with respect to the handle after the needle has been shielded therein.

The proximal portion of the handle is collapsible yet non-elastic so that when the sharp distal tip of the needle extends beyond the distal portion of the handle, the proximal portion is collapsed minimizing the length of the handle extending proximally of the needle hub. This minimizes the length of the assembly thus making it easier for the medical technician to handle the assembly during the procedure for inserting the needle into the patient. In addition, minimizing the length of the assembly facilitates packaging of the assembly by minimizing the amount of material needed and the size of the shipping crates needed. When the medical technician activates the latch withdrawing the needle into the handle, the collapsible proximal portion of the handle extends to its full length under the force of the spring or manually to allow the handle to cover the entire length of the needle. The non-elasticity of the proximal portion prevents it from being stretched and thus, prevents the sharp distal tip of the needle from being moved too far proximally inside the handle.

The tip guard is biased against the needle when the needle extends distally beyond the distal portion of the handle and slides along the shaft of the needle as the proximal portion of the handle extends to its full length. After the proximal portion of the handle extends to the point where the distal tip of the needle is withdrawn into the distal portion of the handle, the tip guard moves toward an unbiased condition over the distal tip of the needle. Thus, the tip guard prevents distal movement of the needle with respect to the handle that could re-expose the distal tip of the used needle.

The proximal portion of the handle could take a number of forms. For example, the proximal portion could be formed from a flexible sleeve of impermeable, non-elastic material with low elongation characteristics, such as polyester, canvas, cloth or thin, flexible metal. Alternatively, the proximal portion of the handle could be formed from telescoping tubes. The tubes should be thin-walled, but sufficiently rigid to prevent kinking and to ensure smooth telescoping movement. Interlocking means between adjacent tubes, such as cooperating flanges on adjacent tubes, are used to prevent complete separation of the telescoping tubes during extension.

BRIEF DESCRIPTION OF THE DRAWINGS

The preferred embodiments are illustrated in the drawings in which like reference numerals refer to like elements and in which:

FIG. 5 is an enlarged cross-sectional view of a portion of the needle shield assembly of this invention showing the resilient tip guard prior to activation of the needle shield mechanism;

FIG. 6 is an enlarged cross-sectional view of a portion of the needle shield assembly of this invention showing the resilient tip guard after activation of the needle shield mechanism;

FIG. 7 is a cross-sectional view of a second embodiment of the needle shield assembly of this invention without the catheter before the needle shield mechanism has been activated; and FIG. 8 is a cross-sectional view of a second embodiment of the needle shield assembly of this invention similar to FIG. 7 but showing the needle enclosed in the assembly after the needle shield mechanism has been activated.

DETAILED DESCRIPTION OF THE INVENTION

Figure 1:
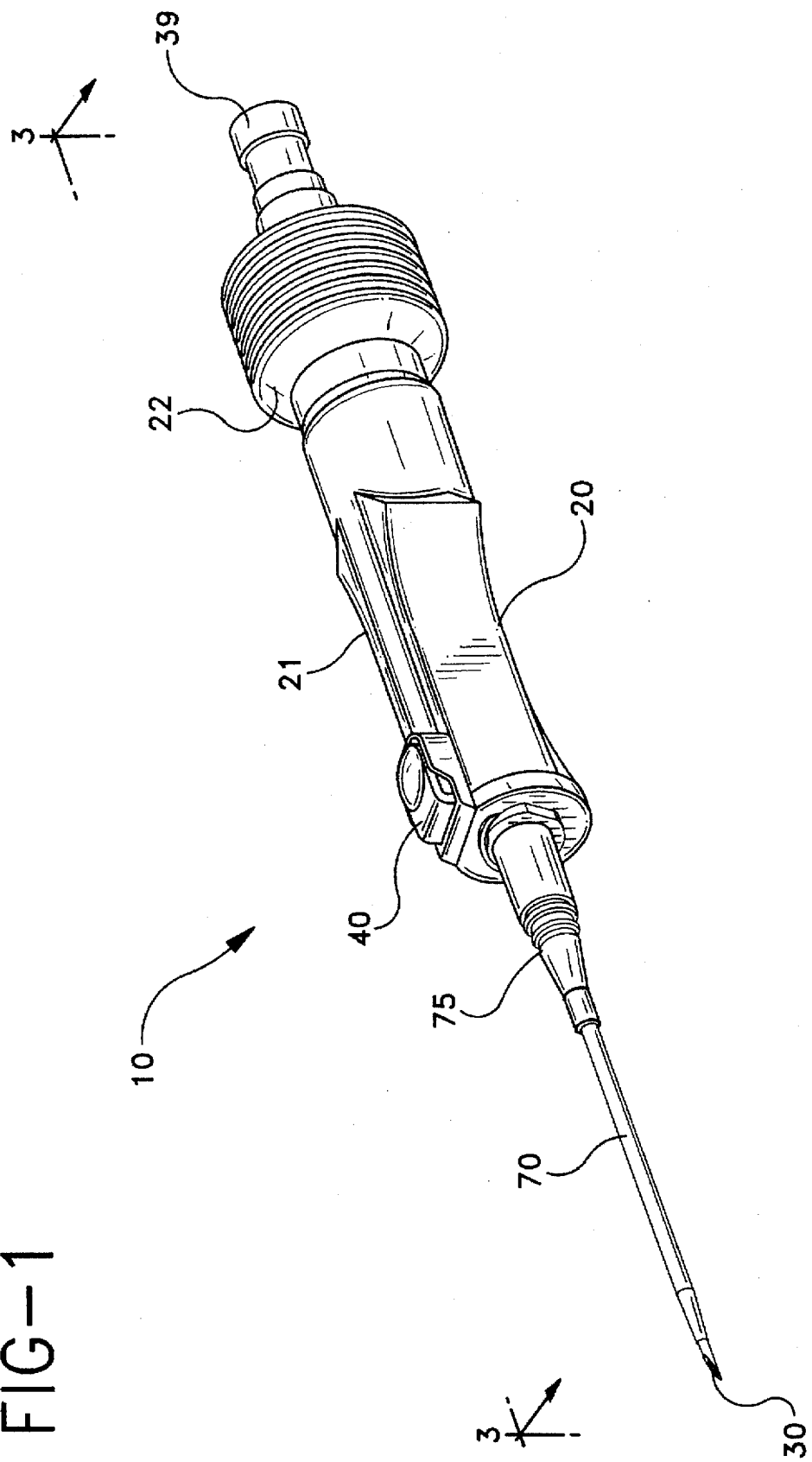
FIG. 1 is a perspective view of the needle shield assembly having a collapsible cover of this invention before the needle shield mechanism has been activated.
Figure 2:
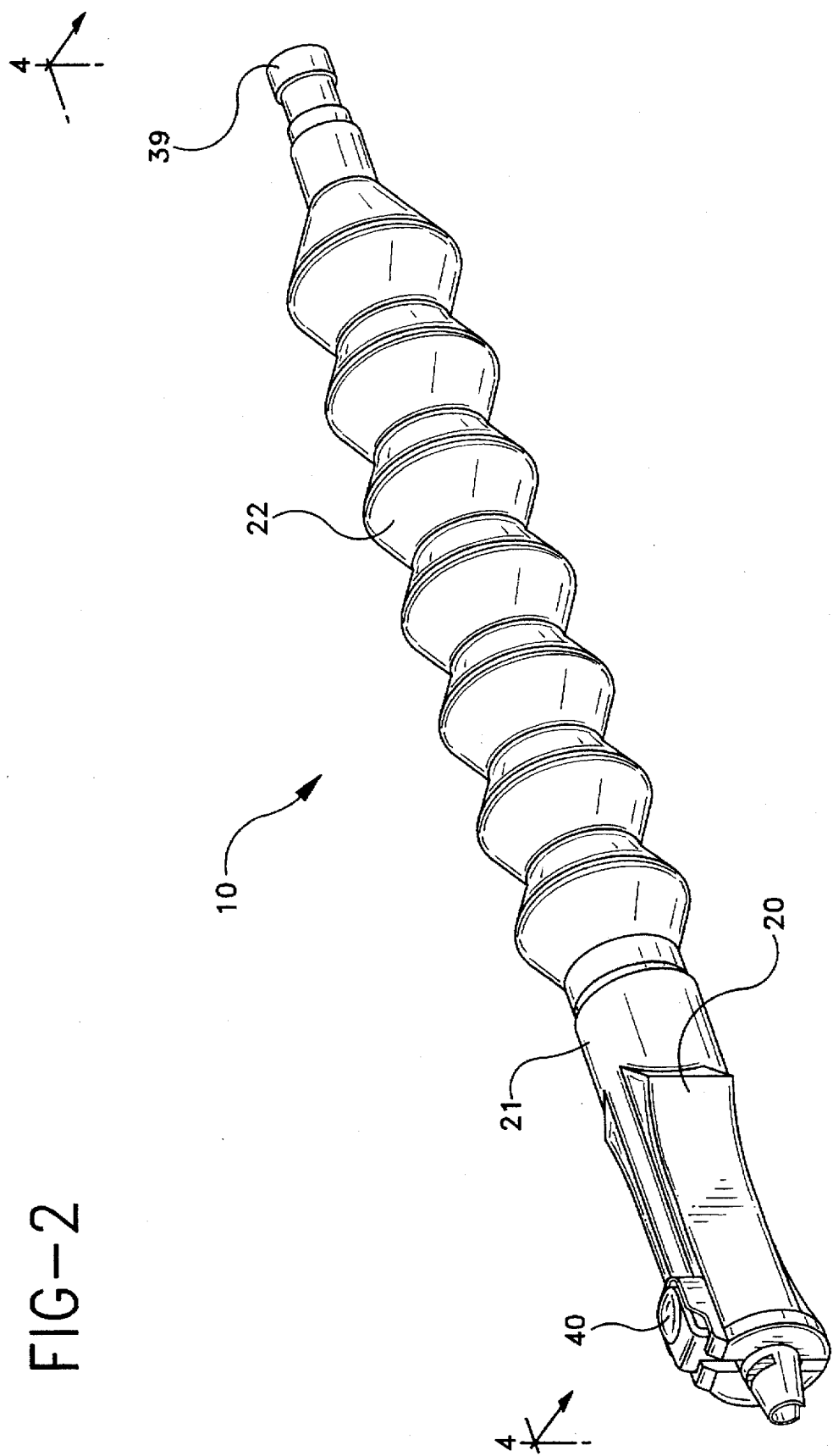
FIG. 2 is a perspective view of the needle shield assembly of FIG. 1 with the needle enclosed in the assembly and the catheter removed after the needle shield mechanism has been activated.

The needle shield assembly 10 of this invention includes a handle 20, a needle 30, a needle hub 35, a latch 40, a spring 50 and a needle tip guard 60. A catheter 70 attached to a catheter hub 75 is located over needle 30. Although this invention is described herein for use with an IV catheter, it is to be understood that the needle shield assembly 10 of this invention could be used with other needles where shielding of the needle is desirable.

Needle hub 35, which can include a flashback chamber, is located inside handle 20. A removable vent plug 39 can be placed in the proximal end of needle hub 35. The removability of vent plug 39 allows a syringe or guidewire (not shown) to be inserted through needle hub 35 and needle 30 into a patient to facilitate placement of catheter 70 into the patient or to otherwise treat the patient.

Needle 30 has a sharp distal tip and is connected at its proximal end to needle hub 35 so that when needle hub 35 is adjacent to the distal end of handle 20, the sharp distal tip of needle 30 extends beyond the distal end of handle 20. Spring 50 is located about needle 30 and between the distal end of handle 20 and needle hub 35 to urge needle 30 toward the proximal end of handle 20. Latch 40 preferably defines a keyhole opening through which needle hub 35 extends so that latch 40 engages needle hub 35 when needle hub 35 is adjacent to the distal end of handle 20 to hold needle hub 35 against the bias of spring 50. When the medical technician desires to shield needle 30 after use, latch 40 can be depressed to allow spring 50 to urge needle hub 35, and thus needle 30, toward the proximal end of handle 20. This withdraws needle 30 into handle 20. Such a latch is disclosed in pending U.S. patent application Ser. No. 08/364, 635 filed on Dec. 27, 1994, the disclosure of which is hereby expressly incorporated by reference.

Handle 20 has a distal portion 21 and a proximal portion 22. Distal portion 21 is formed from a relatively rigid material such as polycarbonate, however, any clean, rigid, medical grade plastic is acceptable. Distal portion 21 should be long enough to house spring 50 and permit viewing of flashback in the flashback chamber portion of needle hub 35. Proximal portion 22 is collapsible and non-elastic. The material used for proximal portion 22 must be sufficiently flexible to allow it to be stored and used in the collapsed state and thereafter to extend but not stretch significantly when the medical technician desires to shield needle 30 in handle 20. In one embodiment shown in FIGS. 1–6, proximal portion 22 is formed from a flexible, impermeable, non-elastic material with low elongation characteristics. Acceptable materials for proximal portion 22 include, polyester, canvas, cloth or thin, flexible metal. Proximal portion 22 is bonded to distal portion 21 by any suitable means such as by using a force fit, ultrasonic welding or the use of a standard adhesive.

Figure 3:
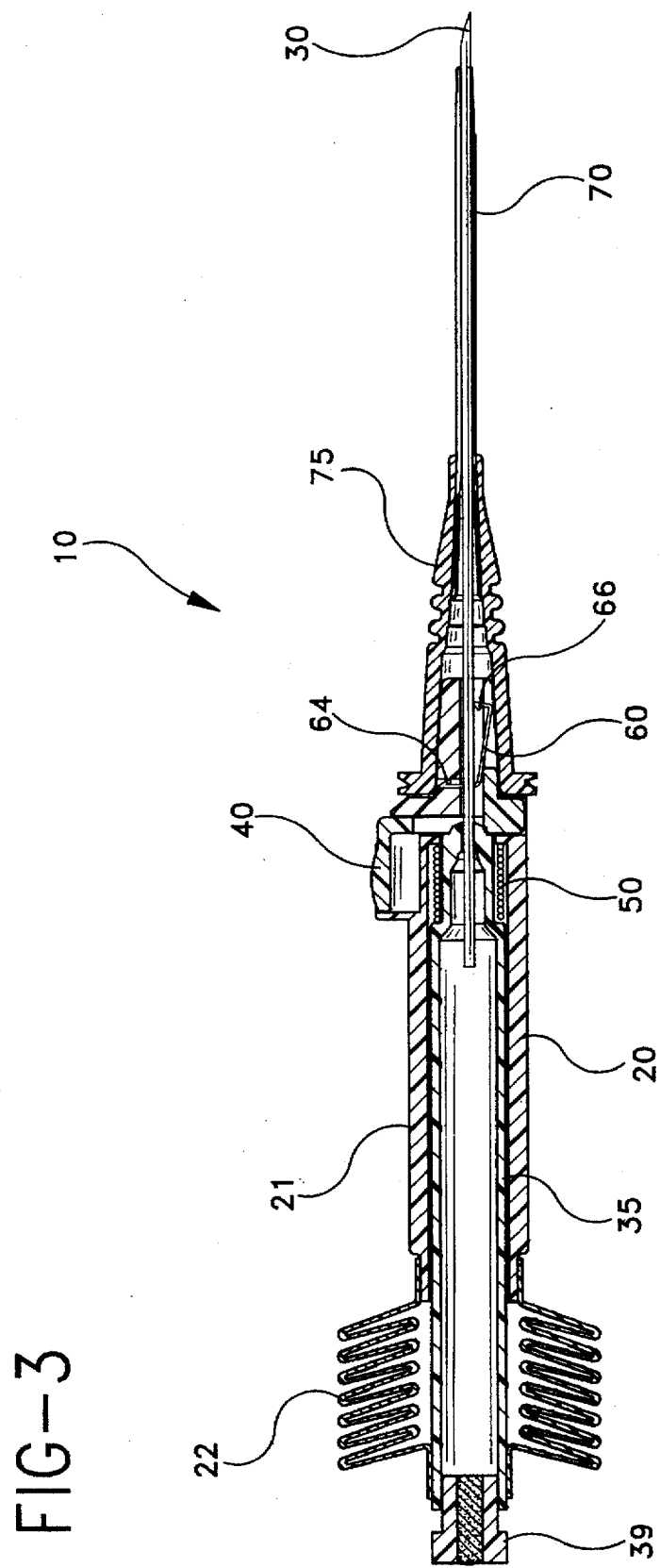
FIG. 3 is a cross-sectional view of the needle shield assembly of this invention prior to activation of the needle shield mechanism.
Figure 4:
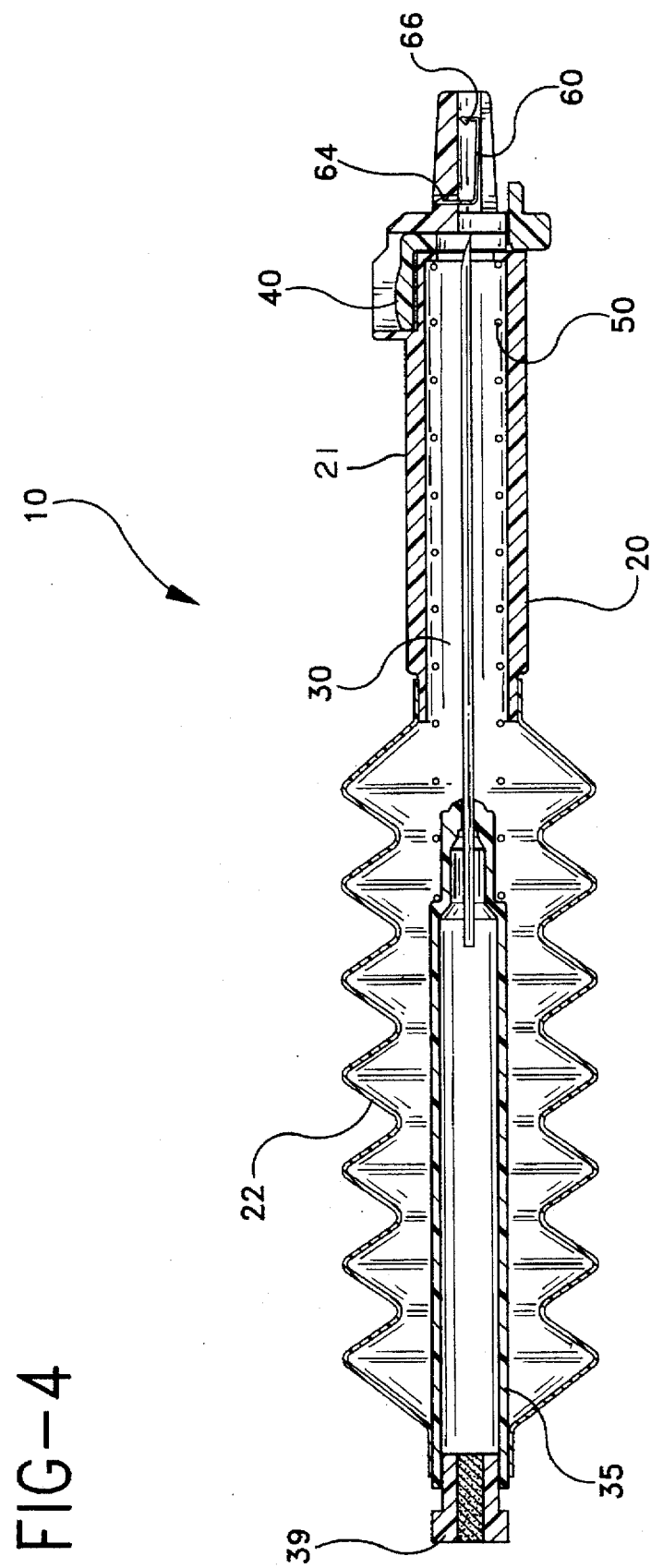
FIG. 4 is a cross-sectional view of the needle shield assembly of this invention similar to FIG. 3 but showing the needle enclosed in the assembly and the catheter removed after the needle shield mechanism has been activated.

When needle hub 35 is adjacent to the distal end of handle 20, proximal portion 22 can be collapsed to thereby minimize the length of proximal portion 22. As seen in FIG. 3, proximal portion 22 preferably has a bellows configuration to facilitate collapsing and extending thereof. It is to be understood that other configurations for proximal portion 22 are acceptable. With proximal portion 22 in its collapsed condition, handle 20 is easier to manipulate when catheter 70 is inserted into a patient via needle 30. After needle 30 has been used to place catheter 70 into a patient and latch 40 is depressed to allow needle 30 to be retracted into handle 20, proximal portion 22 extends as needle hub 35 moves proximally. Proximal portion 22 must have a sufficient length in its fully extended position to allow the sharp distal tip of needle 30 to be withdrawn inside distal portion 21 of handle 20 but must not be too long and must not stretch so as to allow the sharp distal tip of needle 30 to be withdrawn into proximal portion 22. If proximal portion 22 were too long in its fully extended position or if proximal portion 22 were to unduly stretch, the sharp distal tip of needle 30 could become adjacent to proximal portion 22 raising the possibility that needle 30 could puncture the material of proximal portion 22 and expose needle 30. The proximal end of proximal portion 22 is preferably bonded directly to the proximal portion of needle hub 35.

As shown most clearly in FIGS. 5 and 6, needle tip guard 60 is securely mounted in distal portion 21 of handle 20. Needle tip guard 60 is formed from a resilient material, preferably a stainless steel shim, and includes a mounting leg 64 and a shielding leg 66 Mounting leg 64 preferably defines a hole through which needle 30 passes. In the collapsed condition of needle shield assembly 10 shown in FIG. 5, shielding leg 66 is in sliding engagement with the shaft of needle 30 so as to be biased toward the portion of distal portion 21 to which mounting leg 64 is mounted. As needle 30 is moved in a proximal direction, the distal tip thereof will move proximally of shielding leg 66 of needle tip guard 60. At that point, shielding leg 66 will resiliently move toward an undeflected condition and will safely cover the sharp distal tip of needle 20. As shown in FIG. 6, needle 30 could be moved further proximally so as to be proximal of mounting leg 64. Thus, any distal movement of needle 30 relative to handle 20 that could conceivably re-expose needle 30 is prevented by shielding leg 66 of needle tip guard 60.

In a second embodiment of this invention, shown in FIGS. 7 and 8, proximal portion 22 of handle 20 is formed from a telescoping tube 26 that engages a slidable portion 36 of needle hub 35. Slidable portion 36 includes a tongue portion that engages a slot 37 formed in the outer wall of needle hub 35 to allow slidable portion 36 to slide along substantially the entire length of needle hub 35. Preferably tube 26 and slidable portion 36 are formed from stainless steel although other materials such as rigid plastics could be used. Tube 26 and slidable portion 36 each have a wall thickness selected to prevent kinking during the shielding operation, and to ensure smooth telescoping movement. A small wall thickness such as between about 0.002 inches to about 0.005 inches is acceptable.

The distal end of tube 26 is connected directly to the proximal end of distal portion 21. As shown in FIGS. 7 and 8, tube 26 could be threaded onto distal portion 21. Alternative bonding methods could be used or tube 26 and distal portion 21 could be formed as one piece. The proximal end of tube 26 includes an inwardly extending locking flange 26a. The distal end of slidable portion 36 includes an outwardly extending locking flange 36a. Thus when the needle shield mechanism is activated and spring 50 urges needle hub 35 in the proximal direction, slidable portion 36 also moves with needle hub 35 proximally until flanges 26a and 36a engage. At that point, slidable portion 36 slides along slot 37 in needle hub 35 while needle hub 35 continues its proximal movement until needle 30 is safely shielded in distal portion 21. Slot 37 includes a stop at its distal end to prevent continued movement of slidable portion 36.

This particular configuration for the second embodiment minimizes the number of pieces needed to manufacture needle shield assembly 10 and minimizes its bulk. Alternatively, a plurality of nested telescoping tubes could be used to form proximal portion 22 with one end of the plurality of nested telescoping tubes affixed to distal portion 21 and the other end affixed to needle hub 35. The plurality of nested telescoping tubes would be connected to one another by flanges similar to flanges 26a and 36a shown in the second embodiment of FIGS. 7 and 8. It is to be understood that any number of tubes could be used and the telescoping tubes could be telescoped inside of or outside of distal portion 21. The number of tubes chosen will affect the length and diameter of handle 20 when proximal portion 22 is in the collapsed condition for insertion of needle 20 into a patient.

Thus, it is seen that a needle shield assembly is provided that is not bulky, that is simple and easy to use and that completely covers the entire needle as well as the sharp distal tip after use.

I claim:

1. A needle shield, comprising:

a needle having a sharp distal tip and a proximal end;

a needle hub having a proximal end and a distal end affixed to the proximal end of the needle;

a generally hollow handle having a proximal portion and a distal portion, one of the proximal portion or the distal portion being collapsible and non-elastic, the needle hub being disposed in and movably affixed to the generally hollow handle;

a spring engaged with the needle hub to bias the needle hub toward the proximal portion of the handle; and a movable latch engaged with the needle hub to hold the needle hub against the bias of the spring.

2. A needle shield, comprising:

a needle having a sharp distal tip and a proximal end;

a needle hub having a proximal end and a distal end affixed to the proximal end of the needle;

a generally hollow handle having a proximal portion and a distal portion wherein the proximal portion of the hollow handle is collapsible and non-elastic and the needle hub is disposed in and movably affixed to the proximal portion of the hollow handle;

a spring engaged with the needle hub to bias the needle hub toward the proximal portion of the handle; and a movable latch engaged with the needle hub to hold the needle hub against the bias of the spring.

3. The needle shield of claim 2 wherein the proximal portion of the handle is formed from an impermeable flexible material.

4. The needle shield of claim 1 further comprising a flexible tip guard affixed to the distal portion of the handle biased for covering the sharp distal tip of the needle and preventing relative distal movement of the needle after the needle has been withdrawn into the handle.

5. The needle shield of claim 2 further comprising a flexible tip guard affixed to the distal portion of the handle biased for covering the sharp distal tip of the needle and preventing relative distal movement of the needle after the needle has been withdrawn into the handle.

6. The needle shield of claim 3 further comprising a flexible tip guard affixed to the distal portion of the handle biased for covering the sharp distal tip of the needle and preventing relative distal movement of the needle after the needle has been withdrawn into the handle.

7. The needle shield of claim 2 wherein the proximal portion is formed from a tube in sliding relation to the distal portion for telescoping movement between a collapsed condition where the distal end of the needle is exposed and an extended condition where the distal end of the needle is surrounded by the shield.

8. The needle shield of claim 7, wherein the proximal portion and the distal portion are movingly interlocked with one another for preventing complete separation of the proximal portion and the distal portion.

9. The needle shield of claim 7, further comprising a flexible tip guard affixed to the distal portion of the handle biased for covering the sharp distal tip of the needle and preventing relative distal movement of the needle after the needle has been withdrawn into the handle.

10. The needle shield of claim 8, further comprising a flexible tip guard affixed to the distal portion of the handle biased for covering the sharp distal tip of the needle and preventing relative distal movement of the needle after the needle has been withdrawn into the handle.

* * * * *